US 11,752,253 B2

(12) United States Patent
Kharkar et al.

(10) Patent No.: US 11,752,253 B2
(45) Date of Patent: Sep. 12, 2023

(54) NPWT SYSTEM WITH SELECTIVELY CONTROLLABLE AIRFLOW

(71) Applicant: KCI LICENSING, INC., San Antonio, TX (US)

(72) Inventors: Prathamesh Madhav Kharkar, San Antonio, TX (US); Marisa Schmidt, San Antonio, TX (US); Kathleen L. Derrick, San Antonio, TX (US); Diwi L. Allen, San Antonio, TX (US); Nathaniel Young, San Antonio, TX (US); Kristine M. Kieswetter, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 443 days.

(21) Appl. No.: 17/045,630

(22) PCT Filed: Apr. 11, 2019

(86) PCT No.: PCT/US2019/026893
§ 371 (c)(1),
(2) Date: Oct. 6, 2020

(87) PCT Pub. No.: WO2019/200035
PCT Pub. Date: Oct. 17, 2019

(65) Prior Publication Data
US 2021/0162107 A1    Jun. 3, 2021

Related U.S. Application Data

(60) Provisional application No. 62/657,342, filed on Apr. 13, 2018.

(51) Int. Cl.
*A61M 1/00* (2006.01)
*A61F 13/00* (2006.01)
*A61F 13/02* (2006.01)

(52) U.S. Cl.
CPC ....... *A61M 1/964* (2021.05); *A61F 13/00055* (2013.01); *A61F 13/00068* (2013.01);
(Continued)

(58) Field of Classification Search
CPC ........ A61M 1/964; A61M 1/73; A61M 1/912; A61M 1/743; A61M 1/96; A61M 1/982;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Sarah Al Hashimi
*Assistant Examiner* — Hans Kaliher

(57) ABSTRACT

An assembly includes a drape substantially sealable over a wound bed and a trackpad configured to couple a tube to the drape and allow the tube to provide suction to the wound bed. The assembly also includes a vent opening in the drape, a filter coupled to the drape and communicating with the vent opening, a cover coupled to the drape and movable between a first position to cover the vent opening and filter and a second position to uncover the vent opening and the filter, and a fluid indicator coupled to the drape and operable (Continued)

to provide a visual indication that fluid build-up is present in the wound bed.

14 Claims, 5 Drawing Sheets

(52) U.S. Cl.
CPC ............ *A61F 13/0216* (2013.01); *A61M 1/73* (2021.05); *A61M 1/95* (2021.05); *A61M 2205/3324* (2013.01); *A61M 2205/584* (2013.01); *A61M 2205/75* (2013.01)

(58) Field of Classification Search
CPC ......... A61M 2205/584; A61M 2205/75; A61F 13/00068; A61F 13/0216
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0087767 A1* | 4/2010 | McNeil ............ A61F 13/00068 602/42 |
| 2011/0054421 A1* | 3/2011 | Hartwell ............ A61F 13/0216 604/319 |
| 2013/0172836 A1* | 7/2013 | Vess ........................ A61M 1/85 604/319 |
| 2015/0265475 A1* | 9/2015 | Joseph ............. A61F 13/51496 604/361 |
| 2015/0320919 A1* | 11/2015 | Bussett .................... A61M 1/04 604/540 |
| 2016/0262672 A1* | 9/2016 | Hammond .......... A61F 13/8405 |
| 2016/0339155 A1 | 11/2016 | Pratt et al. |
| 2019/0151159 A1* | 5/2019 | Gowans ............. A61F 13/0203 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |

(56) References Cited

FOREIGN PATENT DOCUMENTS

| | | |
|---|---|---|
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2012/012286 A1 | 1/2012 |

OTHER PUBLICATIONS

Susan Mendez-Eatmen, Rn; "When wounds Won't Heal" RN Jan. 1998, vol. 61 (1); Medical Economics Company, Inc., Montvale, NJ, USA; pp. 20-24.

James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Flosure, "Introducing The Ventilation Patch," Oct. 2017 (2 pages).

International Search Report and Written Opinion in International Application No. PCT/US2019/026893, dated Jul. 1, 2019.

* cited by examiner

NPWT SYSTEM WITH SELECTIVELY CONTROLLABLE AIRFLOW

CROSS-REFERENCE TO RELATED APPLICATIONS

This application claims the benefit of priority to international application PCT/US2019/026893, filed Apr. 11, 2019, and U.S. Provisional Application No. 62/657,342, filed on Apr. 13, 2018, the complete disclosures of which are hereby incorporated herein by reference in their entireties.

BACKGROUND

The present disclosure relates generally to wound therapy systems and devices, and more particularly to a drape for use with a negative pressure wound therapy device that provide selectively controllable airflow therethrough.

Negative pressure wound therapy (NPWT) is a type of wound therapy that involves applying negative pressure (relative to atmospheric pressure) to a wound site to promote wound healing. Some NPWT systems include a drape substantially sealed over a wound site and a pump which operates to maintain the wound site at negative pressure and remove wound exudate from the wound site via a tube coupled to the drape. However, wound exudate and other debris can create blockages that restrict fluid from being pulled through the tube, leading to fluid buildup. In some scenarios, improved air flow through the wound site may minimize the possibility of blockages in the connector tube and enhance removal of wound exudate.

SUMMARY

One implementation of the present disclosure relates to an assembly. The assembly includes a drape substantially sealable over a wound bed and a trackpad configured to couple a tube to the drape and allow the tube to provide suction to the wound bed. The assembly also includes a vent opening in the drape, a filter coupled to the drape and communicating with the vent opening, a cover coupled to the drape and movable between a first position to cover the vent opening and filter and a second position to uncover the vent opening and the filter, and a fluid indicator coupled to the drape and operable to provide a visual indication that fluid build-up is present in the wound bed.

In some embodiments, the cover includes a peelable polymer cover. In some embodiments, the peelable polymer cover includes a pressure-sensitive adhesive layer positioned at a bottom surface of the peelable polymer cover. The pressure-sensitive adhesive layer includes one or more of polyacrylate, polymethacrylate, polyurethane, hydrogel, natural rubber, synthetic rubber, styrene block copolymer, polyvinyl ether, polyolefin, hydrocolloid, silicon or silicone based material, styrene butadiene, polyisoprene, polychloroprene, polybutadiene, polychlorosulphonated polyethylene, rosin tackifier, coumarone resin, or coumarone indene resin. In some embodiments, the peelable polymer cover is shaped as one or more of a circle, a triangle, a square, a rectangle, a pentagon, a hexagon, a heptagon, or other polygonal shape. In some embodiments, the peelable polymer cover has an abstract, non-polygonal, or otherwise irregular shape.

In some embodiments, the vent opening includes a plurality of vent openings and the cover comprises a plurality of peelable polymer covers. In some embodiments, the plurality of vent openings and the plurality of peelable polymer covers are disposed in a pattern on the drape to provide a selectively customizable air flow profile beneath the drape. In some embodiments, the vent has a surface area within a range between approximately 0.001 square centimeters and approximately 40 square centimeters, preferably in the range of 0.01 to 1 square centimeter.

In some embodiments, the filter prevents the passage of microbes through the vent opening, prevents backflow through the vent, and allows the flow of air through the vent opening when the cover is in the second position. In some embodiments, the filter is hydrophobic. The filter includes pores with average diameter in a range between approximately 0.1 micron and approximately 0.4 micron and is fabricated from one or more of polyether sulfone, cellulose acetate, cellulose nitrate, nylon, polypropylene, or polytetrafluoroethylene.

In some embodiments, the fluid indicator includes a top layer and a bottom layer. The bottom layer includes a substrate coated with a water-soluble biocompatible colorant (e.g., dye, ink, pigment). The top layer is substantially unpigmented and is configured to allow capillary action from the bottom layer. The capillary action draws the colorant to the top layer when the bottom layer contacts fluid. In some embodiments, the substrate includes one or more of a polymer, a textile, or cellulose. The top layer includes one or more of an absorptive textile or paper. The top layer has a thickness and absorptivity tuned such that a change in color of the top layer corresponds to a predetermined amount of fluid buildup in the wound bed.

In some embodiments, the fluid indicator is also operable to indicate at least one of a pH, a presence of microbes, a presence of matrix metalloproteinases, or a presence of other proteases. In some embodiments, the cover includes the fluid indicator.

In some embodiments, the assembly also includes a plurality of additional vent openings interspersed on the drape and a plurality of additional filters. Each additional filter is coupled to the drape and is communicating with one of the plurality of additional vent openings. The assembly also includes a plurality of additional covers, each additional cover positioned at a corresponding filter of the plurality of additional filters and movable between a closed position to seal the corresponding filter and an open position to unseal the corresponding filter.

In some embodiments, the drape includes perforations that allow for customization of the drape in a plurality of possible shapes. The vent opening and the plurality of additional vent openings are positioned on the drape to provide at least one vent opening for each of the plurality of possible shapes.

In some embodiments, the cover includes a film having perforations or fenestrations that allow air flow to the filter when the cover is in the first position. In some embodiments, the cover includes a valve, for example a one-way valve. In some embodiments, the cover is further moveable to a range of intermediate positions between the first position and the second position. The range of intermediate positions corresponds to a range of air flow rates through the filter.

Another implementation of the present disclosure is a wound dressing assembly. The wound dressing assembly includes a drape configured to cover and seal around a perimeter of a wound bed and a track pad disposed on the drape. The track pad is configured to couple to a tube operable to provide suction to the wound bed. The wound dressing assembly also includes at least one vent opening in the drape and a cover coupled to the drape. The cover is incrementally movable between a sealed position and an unsealed position to permit a selectively controllable amount of an airflow through the vent opening to the track pad. The wound dressing assembly also includes an indicator coupled to an underside of the drape and operable to provide a visual indication that a fluid build-up is present in the wound bed.

In some embodiments, the wound dressing assembly also includes a filter coupled to the drape proximate the vent opening and configured to filter the airflow. In some embodiments, the filter includes a hydrophobic membrane filter. In some embodiments, the fluid indicator is disposed on the drape distal from the track pad and configured to provide a fluid indication proximate an edge of the wound bed.

In some embodiments, the at least one vent opening includes a pattern of perforations or fenestrations, and the cover comprises one or more peelable sheets that are controllably removable in one or more segments to create a desired airflow.

In some embodiments, the indicator is further operable to detect at least one or more of a pH, a presence of microbes, a presence of MMPs and/or other proteases. In some embodiments, the indicator can convey presence of or can vary in colorimetric visualization to provide a threshold indication.

Another implementation of the present disclosure is a wound dressing assembly. The wound dressing assembly includes a drape configured to cover and seal around a perimeter of a wound bed and a track pad disposed on the drape. The track pad is configured to couple to a tube operable to provide suction to the wound bed. A fluid indicator is coupled to an underside of the drape and operable to provide a visual indication that fluid build-up is present in the wound bed. A vent assembly is attachable to the drape and operable to provide an airflow through the drape to the wound bed. The vent assembly includes a flange defining a vent opening, a peelable cover disposed on the flange and incrementally movable between a sealed position and an unsealed position, and an adhesive layer disposed on the flange for attachment to the drape. In some embodiments, the flange includes a projection configured to pierce the drape when the flange is attached to the drape.

Another implementation of the present disclosure is a negative pressure wound therapy system. The negative pressure wound therapy system includes a tube, a pump configured to provide a negative pressure to the tube, and a dressing. The dressing includes a drape substantially sealable over a wound bed, a track pad configured to couple a tube to the drape and allow the tube to provide suction to the wound bed, a vent opening in the drape, a filter coupled to the drape and communicating with the vent opening, a cover movable between a first position to seal the filter and a second position to unseal the filter, and a fluid indicator coupled to the drape and operable to provide an indication that fluid build-up is present in the wound bed. Moving the cover to the second position provides airflow through the vent opening, the wound bed, and the tube, and moving the cover to the first position allows the negative pressure to be substantially maintained in the wound bed. In some embodiments, the cover is further moveable along a range of intermediate positions to adjust a rate of airflow permitted through the vent opening.

DETAILED DESCRIPTION

Figure 1:
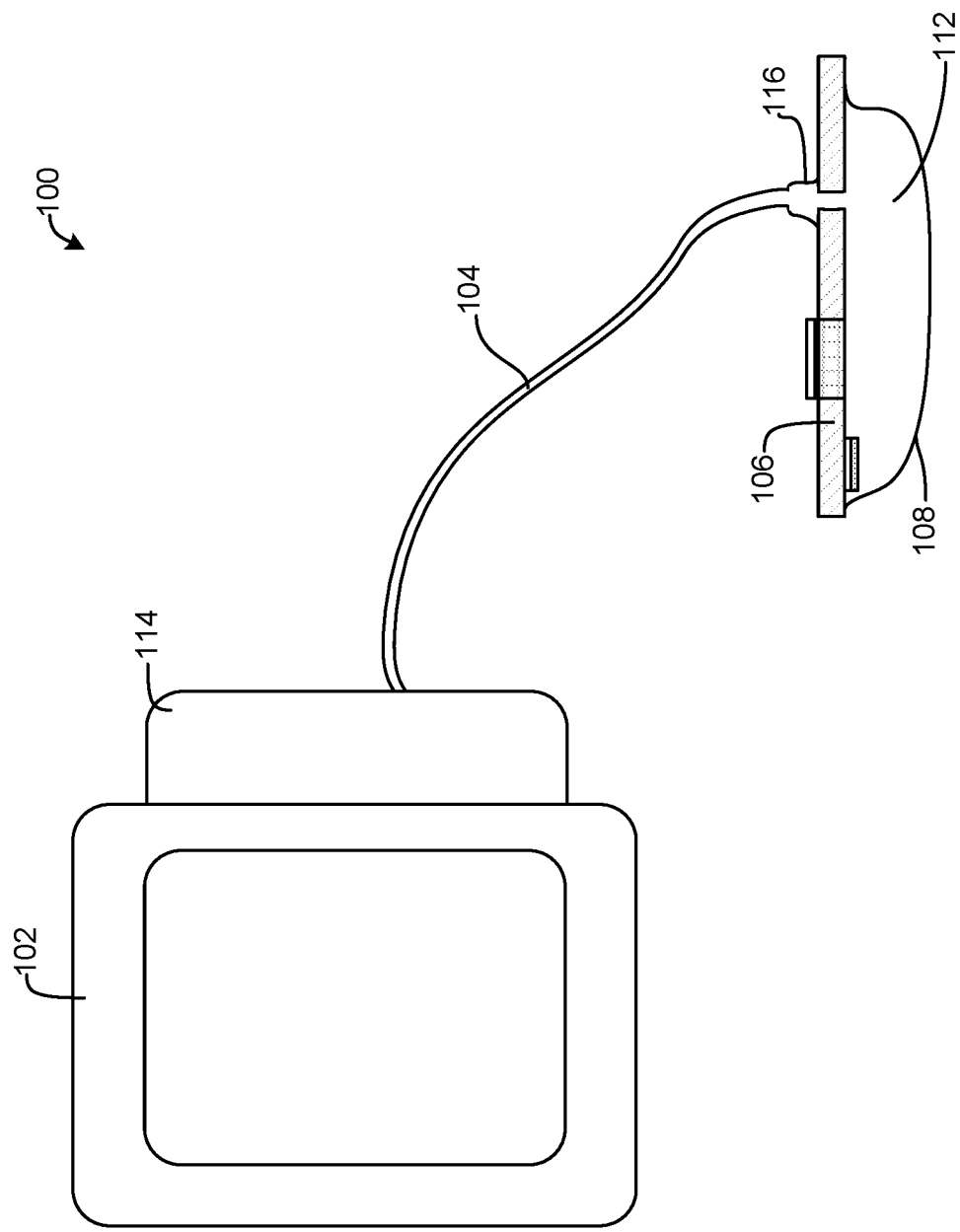
FIG. 1 is a front view of a negative pressure wound therapy system, according to an exemplary embodiment.

Referring to FIG. 1, a negative pressure wound therapy (NPWT) system 100 is shown, according to an exemplary embodiment. NPWT system 100 includes a therapy device 102 fluidly connected via a tube 104 to a drape 106 substantially sealed over a wound bed 108. Wound bed 108 is a typically a tissue wound on a patient, for example a trauma wound, a chronic wound, a third-degree burn, etc. A wound insert 110, for example a foam dressing configured for use with the NPWT system 100, may be positioned in a volume 112 between the wound bed 108 and the drape 106.

Therapy device 102 is configured to provide negative pressure wound therapy by reducing the pressure at wound bed 108. More particularly, therapy device 102 includes a pump (not shown) that can draw a negative pressure (relative to atmospheric pressure) at wound bed 108 by removing wound exudate, air, and other fluids or debris from wound site 108 via tube 104. More particularly, the pump operates to provide a negative pressure to the tube, which causes air and/or fluid to be sucked through the tube and deposited in a canister 114. Wound exudate may include fluid that filters from a patient's circulatory system into lesions or areas of inflammation. For example, wound exudate may include water and dissolved solutes such as blood, plasma proteins, white blood cells, platelets, and red blood cells. Removing fluid from the wound bed 108 helps to minimize fluid pooling in the wound bed 108 and prevent complications associated with maceration in order to promote wound healing. Negative pressure at the wound bed 108 may also increase blood flow to the wound bed, reduce infection risks, and provide other benefits to the patient.

Drape 106 is substantially sealed over the wound bed 106, such that little to no air leaks through or past the drape 106 and into the wound bed 108. Drape 106 thereby facilitates the maintenance of negative pressure in the volume 112 between the drape 106 and the wound bed 108 created by the pump via tube 104. In some cases, however, the seal between the drape 106 and the wound bed 108 is sufficient to create the risk of fluid blockages in the tube 104. For example, the pump may cause a cross-section of the tube 104 to be filled with a fluid. In such a case, a seal is created where the fluid meets the tube 104, such that as the fluid is pulled towards the pump, the pressure drops in the volume 112. At some point, the pressure in the volume 112 becomes equal to or lower than the pressure exerted by the pump, such that the pump no longer pulls the fluid towards the therapy unit 102, creating a blockage. The tube 104 and a trackpad 116 that couples the tube 104 to the drape 106 may include features intended to reduce the risk of such blockages. Another possible solution to fluid blockage in the tube 104 is to provide some amount of air flow to the wound bed 108 that can serve to fill in behind a potential blockage to prevent the pressure in the volume 112 from dropping to or below the pressure exerted by the pump. As described in detail with respect to FIGS. 2-4, the wound dressing assembly described herein is configured to combat fluid blockages and buildup by providing an indication of the presence of fluid buildup in the wound bed 108 and selectively providing microbe-free airflow to the wound bed 108 to facilitate the flow of fluid through the tube 104.

Figure 2:
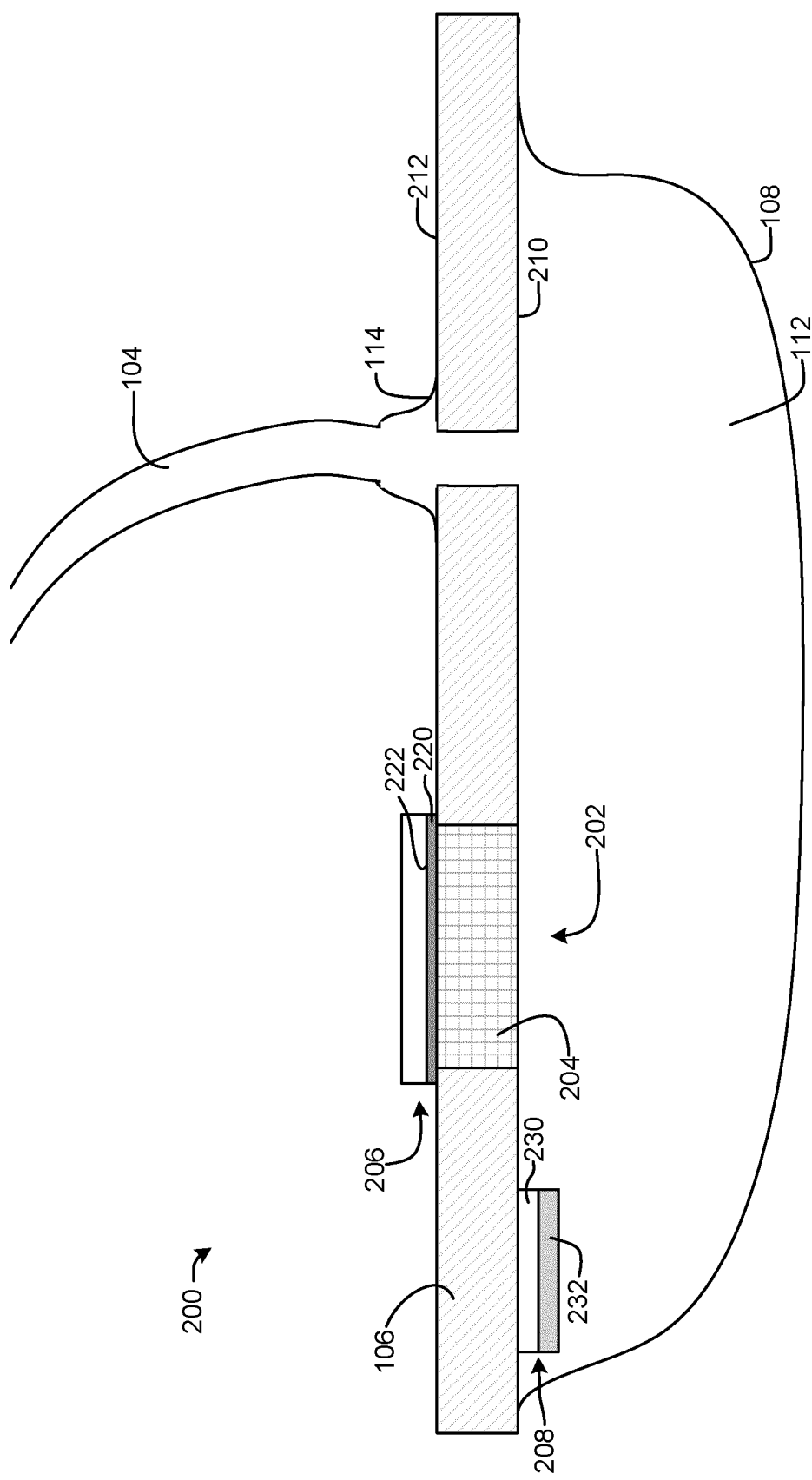
FIG. 2 is a cross-sectional view of a wound dressing assembly for use with the negative pressure wound therapy system of FIG. 1 with a cover in a first position, according to an exemplary embodiment.

Referring now to FIG. 2, a cross-sectional view of a wound dressing assembly 200 with a cover 206 in a closed position is shown, according to an exemplary embodiment. The wound dressing assembly 200 includes a drape 106, a trackpad 114, a vent opening 202, a filter 204, a cover 206, and an indicator 208.

The drape 106 is configured to cover and seal around a perimeter of the wound bed 118. The drape has an inner surface 210 adjacent the volume 112 and an outer surface 212 facing the patient's external environment (e.g., the air surrounding the patient).

The trackpad 114 is configured to couple the tube 104 to the drape 106 and allow the tube 104 to provide suction to the wound bed 108 (i.e., to the volume 112). In some embodiments, the trackpad 114 is integrated into the drape 106. In some embodiments, the trackpad 114 adheres to the outer surface 212 of the drape 106 to align the tube 104 with a hole through the drape 106.

The vent opening 202 extends through the drape 106. According to various embodiments, the vent has a surface area within a range between approximately 0.001 $cm^2$ and approximately 40 $cm^2$. A preferable surface area of the vent opening 202 may be within a range of approximately between 0.01 $cm^2$ and 1 $cm^2$. Smaller or larger surface areas are also possible. The vent opening 202 may be any suitable shape, including a rectangle, circle, ellipse, slit, pentagon, octagon, irregular polygon, etc. While the wound dressing assembly 200 of FIG. 2 shows a single vent opening 202, any number of vent openings 202 may be included in a variety of arrangements, as discussed in detail with reference to FIGS. 4A-D.

Figure 3A:
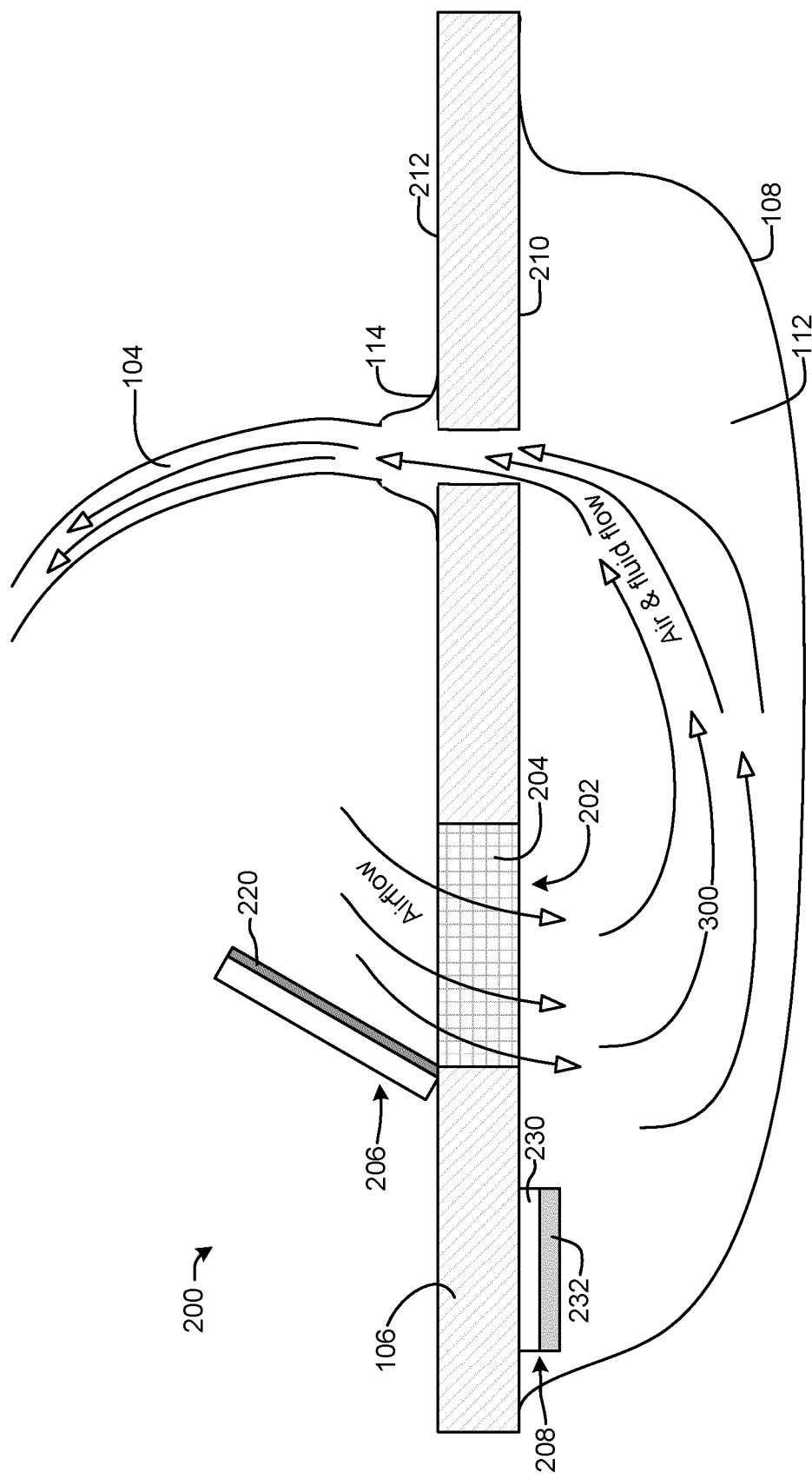
FIG. 3A is a cross-sectional view of the wound dressing assembly of FIG. 2 with the cover in a second position, according to an exemplary embodiment
Figure 3B:
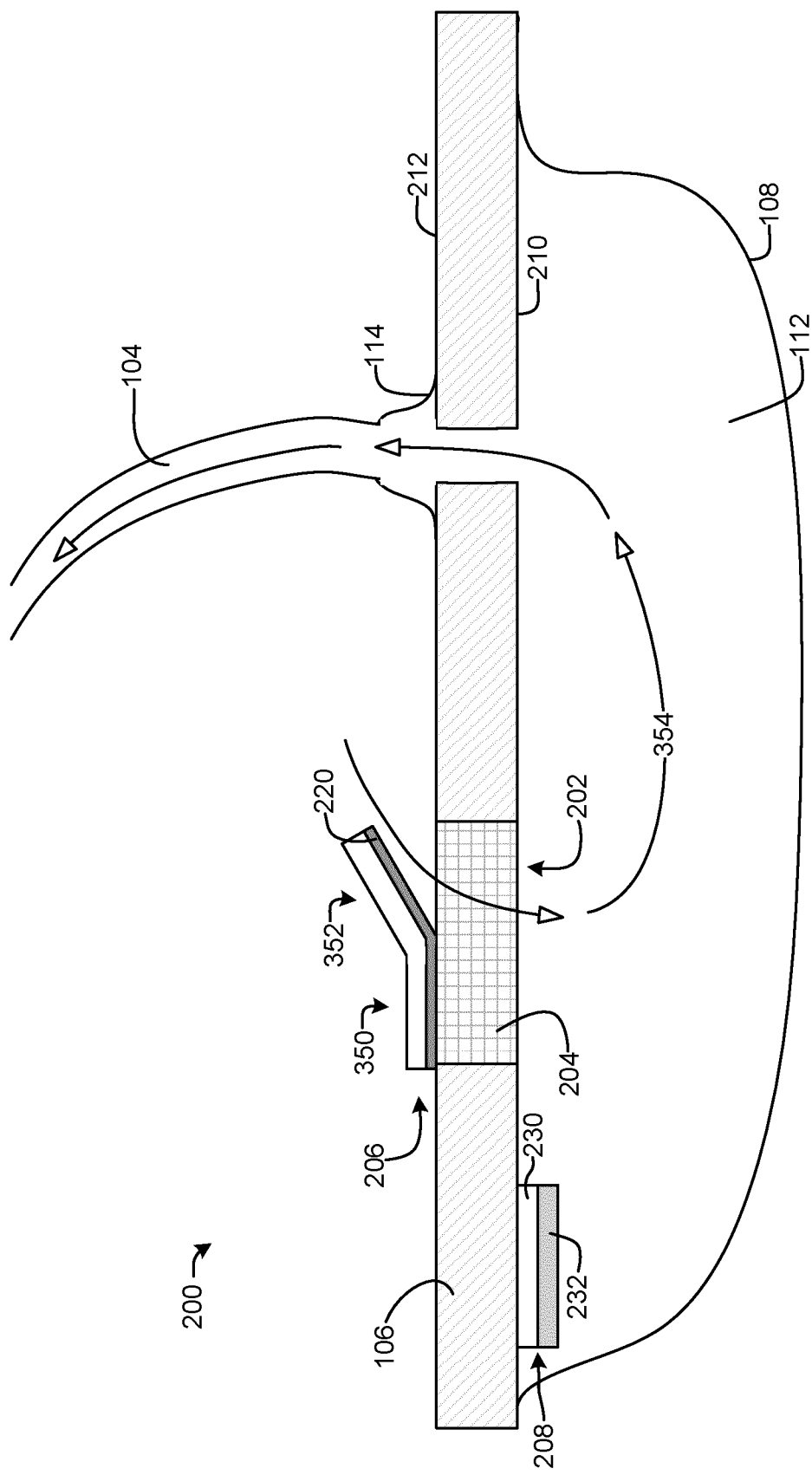
FIG. 3B is a cross-sectional view of the wound dressing assembly of FIG. 2 with the cover in an intermediate position, according to an exemplary embodiment.

The filter 204 is coupled to the drape 106 and is communicable with the vent opening 202. As shown in FIG. 2, the filter 204 fills the vent opening 202, for example aligned with the inner surface 210 and the outer surface 212 of the drape 106. The filter 204 allows the flow of air through the vent opening 202 into the volume 112, for example as illustrated in FIGS. 3A-B, while preventing the passage of microbes or other contaminants through the vent opening 202 and is intended to prevent backflow of air and/or fluid out of the volume 112 through the vent opening 202. Accordingly, the filter is a hydrophobic membrane that includes pores with an average diameter in a range between approximately 0.1 micron and approximately 0.4 micron, preferably between 0.20 and 0.22 micron. The filter may be fabricated from one or more of polyether sulfone, cellulose acetate, cellulose nitrate, nylon, polypropylene, or polytetrafluoroethylene. In an embodiment where the wound dressing assembly 200 includes a plurality of vent openings 202, the wound dressing assembly 200 may also include multiple filters 204, each filter 204 corresponding to one of the vent openings 202.

The cover 206 is positioned proximate the vent opening 202 and the filter 204. More particularly, the cover is coupled to the drape and moveable between a first position (shown in FIG. 2) to cover the vent opening 202 and the filter 204 and a second position (shown in FIG. 3A) to uncover the vent opening 202 and the filter 204. In some embodiments, the cover 206 is also moveable through a range of intermediate positions between the first and second positions, for example as shown in FIG. 3B, to adjust a rate of airflow through the filter 204 and the vent opening 202.

In the embodiments shown in FIGS. 2-4, the cover 206 is a peelable polymer cover manufactured from one or more of polyurethane, polyamide, polypropylene, polyethylene, polyvinyl chloride, ethylene vinyl acetate copolymers, polyvinyl alcohol, or polyether block amide polymers. The cover 206 may be any suitable shape, including a circle, triangle, square, rectangle, pentagon, hexagon, or heptagon, or some combination thereof. In other embodiments, the cover 206 may include, or may be, a valve articulable between an open and closed position.

The cover 206 of FIGS. 2-3D is also shown to include a pressure-sensitive adhesive layer 220 positioned at a bottom surface 222 of the cover 206 that is configured to removably couple the cover 206 to the outer surface 212 of the drape 106 around the vent opening 202. The pressure-sensitive adhesive layer 220 can be pressed against the outer surface 212 to couple the cover 206 to the drape 106, and peeled away from the drape 106 to remove the cover 206 or a portion of the cover 206 from the drape 106. The cover 206 can thereby be repeatedly coupled to and decoupled from the drape 106. In various embodiments, the pressure sensitive adhesive layer 220 is manufactured from one or more of polyacrylate, polymethacrylate, polyurethane, hydrogel, natural rubber, synthetic rubber, styrene block copolymer, polyvinyl ether, polyolefin, hydrocolloid, silicon or silicone based material, styrene butadiene, polyisoprene, polychloroprene, polybutadiene, polychlorosulphonated polyethylene, rosin tackifier, coumarone resin, or coumarone indene resin.

When the adhesive layer 220 adheres the cover 206 to the drape 106 around the vent opening 202 as shown in FIG. 2, the cover 206 substantially seals the vent 202 and the filter 204. A remaining leak rate through the cover 206 (i.e., through the vent opening 202 into the volume 212 when the cover 206 is not in the first position) may vary within a range of between approximately 0.01 and 2 liters per minute, preferably in the range of approximately 0.05 to 0.5 liters per minute. In some cases, the cover 206 includes a film that has perforations or fenestrations that allow air flow to the filter 204 and vent opening 206 when the cover 206 is in the first position (i.e., when the cover is vent opening 206 is 'closed').

Referring further to FIGS. 2-4D, the indicator 208 is coupled to the drape at a strategically advantageous location and is operable to provide a visual indication that fluid build-up is present in the wound bed 108. In some cases, the indicator 208 is additionally or alternatively operable to indicate one or more of a pH, a presence of microbes, a presence of matrix metalloproteinases, or a presence of other proteases.

The indicator 208 includes a top layer 230 and a bottom layer 232. The bottom layer 232 includes a substrate coated with a water-soluble biocompatible colorant (e.g., dye, ink, pigment, etc. with a color of blue, red, green, etc.). The substrate of the bottom layer 232 includes one or more of a polymer, a textile, or cellulose. The top layer 230 is substantially unpigmented and is configured to allow capillary action from the bottom layer. The bottom layer 232 and the top layer 230 are arranged such that when the bottom layer 232 contacts fluid, capillary action draws the colorant to the top layer and causes the top layer to turn the color of the colorant. Accordingly, the top layer 230 is manufactured from one or more of an absorptive textile or paper, with a thickness and absorptivity tuned (e.g. by tailoring the amount of capillary action) such that a change in color of the top layer corresponds to a predetermined amount of fluid buildup in the wound bed. For example, in some cases 0.2 mL of fluid will not turn the top layer 230 the color of the colorant (e.g., blue), but 2 mL of fluid will turn the top layer 230 the color of the colorant. In some embodiments, the top layer 230 is configured to return to an unpigmented appearance after fluid build-up in the wound bed 108 is reduced. The indicator 208 may be configured to show a dichotomous indication of fluid buildup (i.e., fluid or no fluid), or may provide a colorimetric visualization that shows a range fluid levels and may provide a threshold indication.

As shown in FIG. 2, the indicator 208 is coupled to the inner surface 210 of the drape 106. The drape 106 is transparent or translucent such that the color of the top layer 230 of the indicator 208 can be seen through the drape 106. In other embodiments, the indicator 208 extends through the drape 106, such that the top layer 230 is aligned with or protrudes from the outer surface 212 of the drape 106. In some embodiments, the indicator 208 is included with the cover 206 (e.g., coupled to the cover 206, integrated into the cover 206).

The indicator thereby communicates (e.g. by changing color, etc.) to a patient or caregiver that additional airflow is needed to the wound bed 108 to facilitate the removal of fluid via tube 104 to reduce the level of fluid build-up. That is, a change in color of the top layer 230 to the colorant color indicates that a blockage is likely present in the tube 104, which is preventing removal of fluid from the wound bed 108. In response to a change in color of the top layer 230, then, a patient or caregiver may move the cover 206 from the first position (as shown in FIG. 2) to the second position (shown in FIG. 3A and described in detail below) to provide airflow that facilitates the elimination of the blockage.

Referring now to FIG. 3, a cross-sectional view of the wound dressing assembly 200 with the cover 206 in a second position is shown, according to an exemplary embodiment. To transition the cover 206 from the first position shown in FIG. 1, where the adhesive layer 200 substantially seals the cover 206 around the vent opening 202, to the second position shown in FIG. 2, the cover 206 is peeled away from drape 106. The cover 206 may include a tab, grip, flap, etc. to help a patient or caregiver grab the cover 206 and peel the cover 206 away (e.g., pull, un-adhere, decouple) from the drape 106. In some embodiments the cover 206 is securely coupled to the drape 106 at an edge or corner of the cover 206 to allow the cover 206 to be peeled away from the drape 106 as shown in FIG. 2 without completely separating from the drape 106. In other embodiments, the cover 206 is configured to be completely removable from and replaceable on the drape 106.

When the cover 206 is in the second position of FIG. 3A, the vent opening 202 and the filter 204 are uncovered and unsealed. The cover 206 can be selectively moved from the first position to the second position to permit airflow through the vent opening 202 and the filter 204, and replaced in the first position from the second position to substantially prevent airflow through the vent opening 202 to facilitate the maintenance of negative pressure in the volume 112.

FIG. 3A includes flow arrows that illustrate a flow path 300 of airflow through the vent opening 202 and filter 204, across the wound bed 108, and into the tube 104. As air flows through the vent opening 202, the filter 204 filters the air to prevent microbes, moisture, and/or particulates from reaching the wound bed 108. As the filtered air flows across the wound bed 108, fluid and other debris from the wound bed 108 is picked up with it, flowing towards the tube 104. The air and fluid flow is then directed out of the volume 112 through the trackpad 114 and the tube 104 to the therapy unit 104 (shown in FIG. 1). Positioning the cover 206 in the second position thereby facilitates airflow that facilitates movement of fluid from the wound bed 108 towards the tube 104. Furthermore, when the cover 206 is in the second position, the volume 112 is open to a source of air at atmospheric pressure, which substantially prevents the pressure in the volume 112 from dropping to or below the negative pressure created by the pump. Placing the cover 206 in the second position may thereby release a fluid blockage in the tube 104 and/or reduce the risk of future fluid blockages.

A possible scenario may be as follows. A fluid blockage in the tube 104 leads to fluid buildup in the volume 112 (i.e., because the fluid is blocked from removal via tube 104). The top layer 230 of the indicator 208 changes color in response to the fluid buildup, and is noticed by a patient or caregiver. The patient or caregiver then peels the cover 206 from the first position of FIG. 2 to the second position of FIG. 3A, allowing airflow through the vent opening 202 and the filter 204 into the volume 112. Because the volume 112 and the tube 104 are at negative pressure relative to the atmospheric pressure of the outside air, the outside air is pulled through the filter and towards the tube 104, releasing the fluid blockage in the tube 104. The built-up fluid can then also be drawn through the tube 104. At some point, the fluid build-up has been sufficiently reduced, and the cover 206 can be replaced to allow the pump and tube 104 to reestablish a negative pressure in the volume 112.

In some cases, an intermediate level of airflow may be preferable, for example to provide a continuous, consistent, and/or limited air flow. FIG. 3B shows the wound dressing assembly 102 with the cover 206 in an intermediate position, according to an exemplary embodiment. In the intermediate position, the cover 206 covers a portion of the vent opening 202 and the filter 204, while uncovering the remainder of the vent opening 202 and the filter 204. As shown in FIG. 3B, a first portion 350 of the adhesive layer 220 is adhered to the drape 106, blocking airflow to a portion of the vent opening 202 and the filter 204. A second portion 352 of the adhesive layer 220 is peeled away from the drape 106, allowing airflow through the vent opening 202 and filter 204 as indicated by flow path 354.

By changing the relative sizes of the first portion 350 and the second portion 352 (i.e., adhering more or less of the adhesive layer 220 to the drape 106), the cover is incrementally moveable from the first (sealed) position to the second (unsealed) position to permit a selectively controllable or tunable amount of airflow through the vent opening 202 into the volume 102 and to the trackpad 144 and tube 104. For example, an amount of airflow may be chosen that optimally minimizes the risk of fluid blockages and buildup while also allowing a negative pressure to be maintained in the volume 112. Advantageously, the cover 206 is repeatedly moveable through the range of positions corresponding to a range of airflow rates, such that airflow can be repeatedly tuned, or adjusted, for example on a set schedule, in response to an indication of the indicator 208, to adjust to changing wound conditions as healing occurs, to experiment to find an ideal airflow rate for a particular wound and patient, and to allow the wound assembly 106 to be used with a variety of wounds types, wound sizes, and patients. For example, the cover 206 is repositionable to reseal the vent opening 202 after the fluid buildup or liquid pooling has been substantially eliminated by the increased airflow. As discussed with reference to FIGS. 4A-D, similar advantages are achievable using multiple covers 206.

Referring now to FIGS. 4A-D, top views of a variety of possible arrangements of the elements of the wound dressing assembly 200 are shown, according to exemplary embodiments. In general, the present disclosure contemplates any arrangement of one or more trackpads 114, one or more vent openings 202, one or more filters 204, one or more covers 206, and/or one or more fluid indicators 208 on drapes 106 of various shapes and sizes. FIGS. 4A-D illustrate several such arrangements.

Figure 4A:
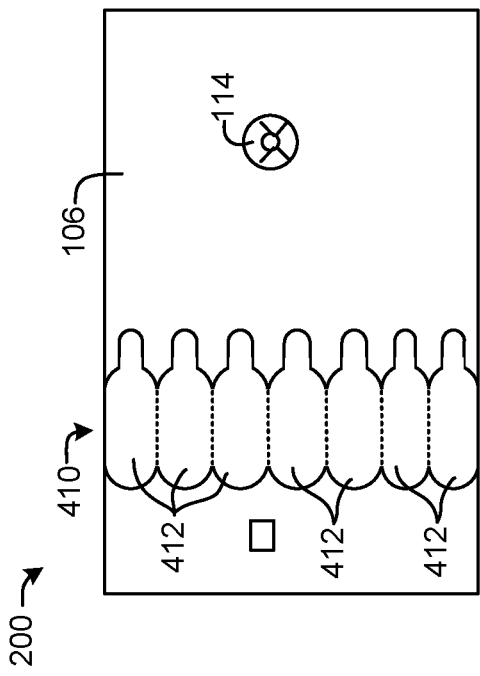
FIGS. 4A-D are top views of various arrangements of the elements of the wound dressing assembly of FIG. 2, according to exemplary embodiments.

FIG. 4A shows the indicator 208 strategically disposed on the drape 106 at a location distal from the track pad 114. In other words, the indicator 208 is separated from the track pad 114 by a large proportion of distance on the drape 106. The indicator 208 is positioned and configured to provide a fluid indication proximate an edge of the wound bed 108. The trackpad 114 is positioned across the wound bed 108 (e.g., along an opposite edge, near an opposing corner), such that the fluid indication provided by the indicator 208 corresponds to fluid buildup in an area of the wound bed 108 far from the trackpad 114. The cover 206 is located near the indicator 208, and covers a vent opening 202 and a filter 204. The cover 206 may be peeled away from the drape 106 to provide airflow to the wound bed 108 proximate the indicator 208.

Figure 4B:
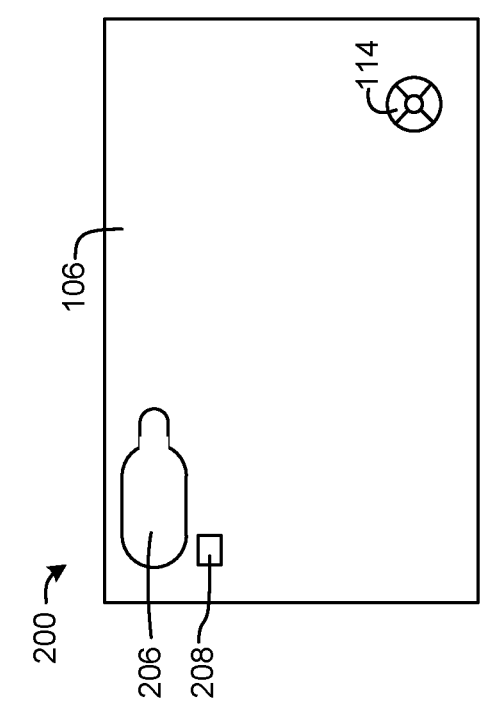

In FIG. 4B, the cover 206 is shown according to another embodiment as a cover strip 410. The cover strip 410 may cover a series of vent openings 202, a single vent opening 202 that extends under the strip of covers 410, or a vent opening 202 made up of a pattern of perforations or fenestrations disposed under the strip of covers 410. The cover strip 410 is shown by way of example to include multiple peelable sheets 412 that are controllably removable in one or more segments to create a desired airflow, in combination with the nature of openings disposed therebeneath (e.g. series of openings, an elongated opening, a plurality of perforations or fenestrations, etc.). The peelable sheets 412 are separated by perforations, such that each peelable sheet 412 is independently movable from a sealed position to an unsealed position to provide airflow to a vent opening 202 or a segment of a vent opening 202 disposed under that peelable sheet 412. Airflow direction and rates can thus be selectively tuned and customized, e.g. in response to an indication of the presence or absence of fluid in the wound bed from indicator 208, by unsealing various combinations of the peelable sheets 412 that make up cover strip 410.

Figure 4C:
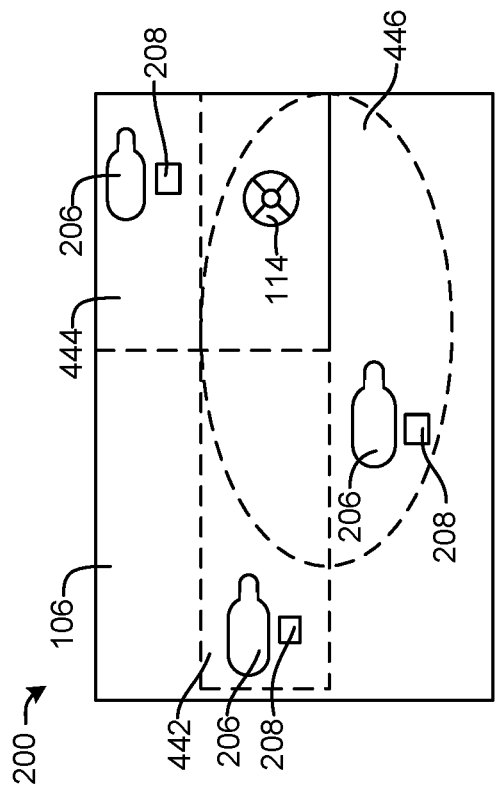

In FIG. 4C, the trackpad 114 is shown by way of example to be centrally located on the drape 106. Multiple vent openings 202 are each covered by a cover 206. As shown, four vent openings 202, each with a corresponding filter 204, are covered by four peelable polymer covers 206. The vent openings 202 and the covers 206 are disposed in a pattern on the drape 106 to provide a selectively customizable air flow profile beneath the drape 106 (i.e., in volume 206). That is, each of the multiple covers 206 can be moved between a closed position to seal the corresponding vent opening 202 and filter 204, an open position to unseal the corresponding vent opening 202 and filter 204, and a range of intermediate positions in between. Multiple indicators 208 are provided to deliver indications of fluid buildup under various locations of the drape 106, which may be useful in selectively tuning the location nand amount of airflow using selected locations and positions (e.g. open, closed, intermediate open, etc.) of the multiple covers 206.

Figure 4D:
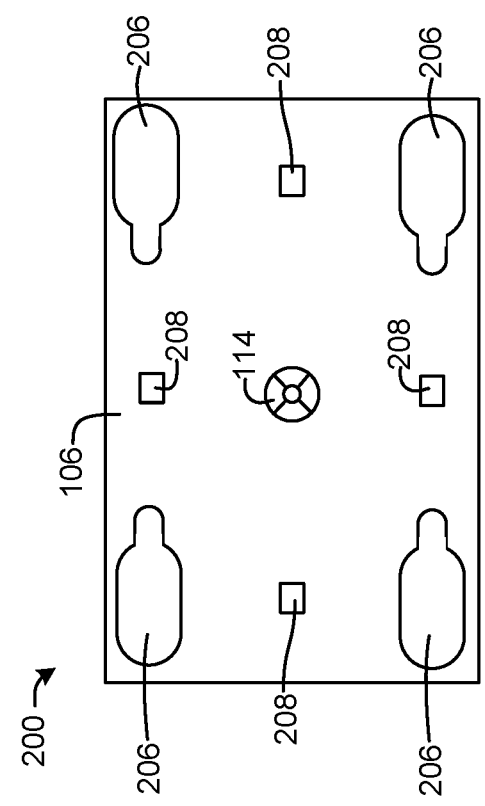

In FIG. 4D, the drape 106 is shown by way of example to include dashed lines (or in some embodiments, perforations 440). Perforations 440 are intended to allow for customization of the drape in multiple possible shapes and/or sizes, shown as a rectangle 442, a square 444, and an oval 446. Several vent openings 202 and covers 206, and indicators 208 are positioned on the drape 106 to provide at least one vent opening for each of the possible shapes 442-444. Thus, the drape 106 of FIG. 4D provides customizability of drape size and shape as well as airflow. For example, the drape may be separated or cut along any of the dashed lines or perforations for adaptation to a shape of a particular wound bed.

Other possible implementations of the wound dressing assembly 200 are possible. For example, in some embodiments a vent assembly is attachable to the drape 106 to selectively position the vent assembly. In such embodiments, the vent assembly includes a flange defining a vent opening, a peelable cover disposed on the flange and incrementally moveable between a sealed position and an unsealed position, and an adhesive layer disposed on the flange for attachment to the drape. The flange may include a projection configured to pierce the drape when the flange is attached to the drape, creating an opening through the drape. One or more of such vent assemblies can be positioned by a user anywhere on the drape 106 to provide the desired selectable airflow. An indicator may be included with the drape 106 as described above, included with the vent assembly, or independently positionable on the drape 106.

According to any exemplary embodiment, a wound dressing for a NPWT system is provided that permits a selectively tunable flow of filtered air through and beneath a drape, in response to an indication of the presence or absence of a fluid buildup in the wound bed. The dressing typically includes a drape, a tube and track pad integrated with the drape and communicating with a negative pressure source, a vent opening (or pattern of vent openings of various shapes and/or sizes) and having a hydrophobic filter disposed in airflow communication therewith, and a fluid indicator coupled to the drape at strategic locations intended to permit a caregiver to assess the location and amount of fluid buildup occurring within the wound bed. The features of the wound dressing permit a controlled airflow through and beneath the drape, in coordination with the capacity of the negative pressure therapy device and the rate (or rate of change of) fluid build-up in the wound bed. A method of selectively tuning an airflow in a negative pressure wound dressing is also disclosed. The method includes at least the steps of observing via one or more indicators the presence or absence of a fluid buildup condition with a wound bed, and establishing a controlled airflow through a drape of the dressing in response to the observation. A method of making a selectively tunable, negative pressure wound therapy dressing is also disclosed. The method includes the steps of providing a drape, coupling one or more fluid indicators to the drape, and providing one or more vent openings that are selectively and/or incrementally openable to establish an airflow in response to an indication from the indicators representative of a fluid buildup. All such variations are intended to be within the scope of this disclosure.

Other arrangements and combinations of the elements described herein and shown in the Figures are also contemplated by the present disclosure. The construction and arrangement of the systems and apparatuses as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. Other substitutions, modifications, changes, and omissions can be made in the design, operating conditions and arrangement of the exemplary embodiments without departing from the scope of the present disclosure.

What is claimed is:

1. An assembly comprising:
a drape substantially sealable over a wound bed;
a track pad configured to couple a tube to the drape and allow the tube to provide suction to the wound bed;
a vent opening in the drape;
a filter coupled to the drape and communicating with the vent opening;
a cover coupled to the drape and movable between a first position to cover the vent opening and filter, and a second position to uncover the vent opening and the filter; and
a fluid indicator coupled to the drape and operable to provide a visual indication that fluid build-up is present in the wound bed, the fluid indicator comprising:
a bottom layer comprising a substrate coated with a water-soluble biocompatible colorant, and
a top layer substantially unpigmented and configured to allow capillary action from the bottom layer, the capillary action drawing the colorant to the top layer when the bottom layer contacts fluid.

2. The assembly of claim 1, wherein the cover comprises a peelable polymer cover.

3. The assembly of claim 2, wherein the peelable polymer cover comprises a pressure-sensitive adhesive layer positioned at a bottom surface of the peelable polymer cover, the pressure-sensitive adhesive layer comprising one or more of polyacrylate, polymethacrylate, polyurethane, hydrogel, natural rubber, synthetic rubber, styrene block copolymer, polyvinyl ether, polyolefin, hydrocolloid, silicon or silicone based material, styrene butadiene, polyisoprene, polychloroprene, polybutadiene, polychlorosulphonated polyethylene, rosin tackifier, coumarone resin, or coumarone indene resin.

4. The assembly of claim 2, wherein the peelable polymer cover comprises one or more of polyurethane, polyamide, polypropylene, polyethylene, polyvinyl chloride, ethylene vinyl acetate copolymers, polyvinyl alcohol, or polyether block amide polymers.

5. The assembly of claim 1, wherein the vent opening comprises a plurality of vent openings and the cover comprises a plurality of peelable polymer covers.

6. The assembly of claim 5, wherein the plurality of vent openings and the plurality of peelable polymer covers are disposed in a pattern on the drape, to provide a selectively customizable air flow profile beneath the drape.

7. The assembly of claim 1, wherein the filter prevents the passage of microbes through the vent opening, prevents backflow through the vent, and allows the flow of air through the vent opening when the cover is in the second position.

8. The assembly of claim 1, wherein the filter is hydrophobic, and comprises pores with average diameter in a range between approximately 0.1 micron and approximately 0.4 micron, and is fabricated from one or more of polyether sulfone, cellulose acetate, cellulose nitrate, nylon, polypropylene, or polytetrafluoroethylene.

9. The assembly of claim 1, wherein:
the substrate comprises one or more of a polymer, a textile, or cellulose; the top layer comprises one or more of an absorptive textile or paper; and
the top layer has a thickness and absorptivity tuned such that a change in color of the top layer corresponds to a predetermined amount of fluid buildup in the wound bed.

10. The assembly of claim 1, wherein the fluid indicator is further operable to indicate at least one of a pH, a presence of microbes, a presence of matrix metalloproteinases, or a presence of other proteases.

11. The assembly of claim 1, further comprising:
a plurality of additional vent openings interspersed on the drape;
a plurality of additional filters, each additional filter coupled to the drape and communicating with one of the plurality of additional vent openings; and
a plurality of additional covers, each additional cover positioned at a corresponding filter of the plurality of additional filters and movable between a closed position to seal the corresponding filter and an open position to unseal the corresponding filter.

12. The assembly of claim 11, wherein the drape comprises perforations that allow for customization of the drape in a plurality of possible shapes, the vent opening and the plurality of additional vent openings positioned on the drape to provide at least one vent opening for each of the plurality of possible shapes.

13. The assembly of claim 1, wherein the cover comprises a film having perforations or fenestrations that allow air flow to the filter when the cover is in the first position.

14. The assembly of claim 1, the cover further moveable to a range of intermediate positions between the first position and the second position, the range of intermediate positions corresponding to a range of air flow rates through the filter.

* * * * *

UNITED STATES PATENT AND TRADEMARK OFFICE
CERTIFICATE OF CORRECTION

PATENT NO. : 11,752,253 B2
APPLICATION NO. : 17/045630
DATED : September 12, 2023
INVENTOR(S) : Prathamesh Madhav Kharkar et al.

It is certified that error appears in the above-identified patent and that said Letters Patent is hereby corrected as shown below:

In the Claims

Column 11
Line 40-41, In Claim 3, delete "polychlorprene" and insert -- polychloroprene --, therefor.

Signed and Sealed this
Ninth Day of April, 2024

Katherine Kelly Vidal
*Director of the United States Patent and Trademark Office*